(12) United States Patent
Zagury et al.

(10) Patent No.: US 7,504,479 B2
(45) Date of Patent: Mar. 17, 2009

(54) USE OF IMMUNOGENIC IMMUNOSUPPRESSIVE AND/OR ANGIOGENIC PROTEINS WHICH HAVE BEEN RENDERED INACTIVE, PROCESS FOR THEIR PREPARATION AND PHARMACEUTICAL OR VACCINAL USES

(75) Inventors: Daniel A. Zagury, Paris (FR); Jean-François Zagury, Paris (FR)

(73) Assignee: Neovacs, Paris (FR)

( * ) Notice: Subject to any disclaimer, the term of this patent is extended or adjusted under 35 U.S.C. 154(b) by 172 days.

(21) Appl. No.: 11/302,285

(22) Filed: Dec. 14, 2005

(65) Prior Publication Data

US 2006/0153862 A1 Jul. 13, 2006

Related U.S. Application Data

(62) Division of application No. 10/465,645, filed on Jun. 20, 2003, now Pat. No. 7,022,482, which is a division of application No. 09/743,700, filed as application No. PCT/FR99/01423 on Jun. 15, 1999, now abandoned.

(30) Foreign Application Priority Data

Jul. 15, 1998 (FR) .................................. 98 09046

(51) Int. Cl.
*A61K 38/00* (2006.01)
(52) U.S. Cl. ..................................................... 530/300
(58) Field of Classification Search ............... 424/204.1; 530/300
See application file for complete search history.

(56) References Cited

U.S. PATENT DOCUMENTS

| 5,308,612 A | 5/1994 | Lee | |
|---|---|---|---|
| 5,547,846 A * | 8/1996 | Bartsch et al. | ................ 435/7.1 |
| 5,753,233 A * | 5/1998 | Bleul et al. | ............... 424/204.1 |
| 5,874,089 A | 2/1999 | Schlegel et al. | |
| 6,093,405 A | 7/2000 | Zagury et al. | |
| 6,132,721 A | 10/2000 | Zagury et al. | |
| 6,200,575 B1 | 3/2001 | Zagury et al. | |
| 6,306,397 B1 * | 10/2001 | Edwards et al. | .......... 424/192.1 |
| 6,420,141 B1 | 7/2002 | Zagury et al. | |
| 6,455,045 B1 | 9/2002 | Zagury et al. | |

FOREIGN PATENT DOCUMENTS

| WO | WO95/31999 | 11/1995 |
|---|---|---|
| WO | WO96/27389 | 3/1996 |

OTHER PUBLICATIONS

"Chemical Abstracts", vik, 130, No. 21 1999 Columbus, Ohihio, US; abstract No. 280480, A. Gringeri et al.; Safety and immunogenicity of HIV-1 Tat toxoid in immunocompromised HIV-1-infected patients.; XP002114179.

J. Rappaport et al.: "HIV-1 Tat toxoid: Rationale for a Tat vaccine and results of a phase I clinical trial." Jornal of Neurovirology, vol. 4, No. 3, Apr. 1996, pp. 97-103, XP002106209.
M. Boursnell et al.; "Construction and characterization of a recombinant vaccinia virus expressing human papillomavirus proteins for immuntherapy of servical cancer." Vaccine, vol. 14 No. 16, Nov. 1998. pp. 1485-1494, XP002106210.
Y. Tanaka et al.: "Production of a recombinant human T-cell leukemia virus type_I trans-activator (tax1) antigen and its util\ization for generation of monoclonal antibodies against various epitipes on the tax1 antigen." International Journal of Cancer, vol. 48, No. 4, Jun. 19, 1991, pp. 623-630, XP002106211.
K. Speidel et al: "Priming of cytotoxic T lymphocytes by five heat-aggregated antigents in vivo: conditions, efficiency, and relation to antibody responses," European Journal of Imunology, vol. 27, No. 9, Sep. 1997, pp. 239102399, XP002106212.
H.Le Buanec et al.: "A prophylactic and therapeutic AIDS vaccine containing as a component the innocuous Tat toxoid." Biomedicine and Pharmacotherapy, vol. 52, No. 10, 1998 pp. 431-435, XP002106213.
A. Gringeri et al.: "Tat toxoid as a compo9nent of a preventive vaccine in seronegative subjects." Journal of Acuired Immune Deficiciency Syndromes and Human Retrovirology, vol. 20, No. 4, Apr. 1, 1999 pp. 371-375, XP002106214.
Murphy et al., Fields Virology, 1990 2nd Ed., Chapter 19, pp. 480-482.
Greenstone et al., Chimeric papillomavirus virus-like particles elicit antitumor immunity against the E7 oncoprotein in an HPV16 tumor model, Proc. Natl. Acad. Sci. USA, 95:1800-1805 (1998).
Wang-Johanning et al., Intracellular expression of a single-shain antibody directed against human papillomavirus type 16E7 oncoprotein achieves targeted antineoplastic effects, Cancer Res. 58(9):1893-1900 (1998).
Asano et al., Inhibition of tumor growth and metastasis by an immunoneutralizing monoclonal antibody to human vascular endothelial growth factor/vascular permeability factor 121, Cancer Res., 55(22):5296-5301 (1995).
Borysiewicz et al., A recombinant vaccinia virus encoding human papillomavirus types 16 and 18, E6 and E7 proteins as immunotherapy for cervical cancer, Lancet, 347(9014):1523-1527 (1996).
Herd et al., E7 oncoprotein of human papillomavirus type 16 expresse constitutitively in the epidermis has no effect on E7-specific B- or Th-repertoires or on the immune response induced or sustained after immunization with E7 protein, Virology, 231(1):155-165 (1997).
Harbiharan et al., Tumor regression in mice following vaccination with human papillomavirus E7 recombinant protein in Provax, Int. J. Oncol., 12(6):1229-1235 (1998).

* cited by examiner

*Primary Examiner*—Ali R. Salimi
(74) *Attorney, Agent, or Firm*—Browdy and Neimark, P.L.L.C.

(57) ABSTRACT

An immunogenic polypeptide for inducing antibodies that neutralize the immunosuppressive and/or angiogenic activity of an E7 protein from Papillomavirus, wherein said immunogenic polypeptide consists of an E7 protein from Papillomavirus that has been inactivated so as to eliminate at least 70% of the immunosuppressive and/or angiogenic activity of the non-inactivated E7 protein. The inactivation is effected by physical and/or chemical treatments and/or by modification of the amino acid sequence of the polypeptide.

14 Claims, 5 Drawing Sheets

USE OF IMMUNOGENIC IMMUNOSUPPRESSIVE AND/OR ANGIOGENIC PROTEINS WHICH HAVE BEEN RENDERED INACTIVE, PROCESS FOR THEIR PREPARATION AND PHARMACEUTICAL OR VACCINAL USES

The present application is a divisional of application Ser. No. 10/465,645, filed Jun. 20, 2003 now U.S. Pat. No. 7,022,482, which is a divisional of application Ser. No. 09/743,700, filed on Jun. 16, 2001 which is a 371 national stage application of PCT/FR99/01423 filed Jun. 15, 1999, and the entire contents of prior application Ser. Nos. 09/743,700, 10/465,645 and PCT/FR99/01423 are herein incorporated by reference.

The present invention relates to the use of immunogenic immunosuppressive and/or angiogenic proteins which have been rendered inactive, a process for their preparation and their pharmaceutical or vaccinal uses.

Active compounds to combat cancer, which is the major medical scourge of our time, are constantly being sought. Numerous therapies have been developed with varying success, since there is still a high mortality. These therapies were initially surgical excision for solid tumours, radiotherapy and chemotherapy. These therapies seem insufficient in the case of several cancers, for which no clinical success indicating a significant prolonging of the survival of the patients or their total recovery has been recorded.

Cancers are proliferations of cells which can subsequently spread in the organism to form metastases. It is known that the immune system of a normal individual regularly eliminates budding cancer cells (immunosurveillance concept) and that the formation of a cancer is associated 1) with escape from the local immunosurveillance system and then with an advanced period of cancer, to systemic immunosuppression, and 2) with a proliferation of vascular endothelial cells ensuring supply of nutrients to the tumour cells (neoangiogenesis).

The majority of anticancer agents (chemotherapy, radiotherapy) used to date combat replication of cancer cells. These agents do not target the particular environment necessary for proliferation of cancer cells, characterized both by the absence of local activity (paracrine) of antitumoral immunity cells (immune escape) and by the occurrence of an intratumoral vascularization (neoangiogenesis).

New therapy approaches have therefore recently been introduced. Some are aimed at stimulating the antitumor immune system by cell therapy or by activation of genes which code for proteins which stimulate the immune response (gene therapy), or by direct immunization against antigens, identified as specific or associated, of the tumour of the MAGE type (vaccination). Others are aimed at combating neoangiogenesis using antimetabolites which destroy the endothelial cells (Judah Folkman). In this new context it is to be noted that De Bruijn et al. (Cancer Res. (1998) 58, pages 724-731) have described the use of the native proteins E6 and E7 to induce a cytotoxic cell response (CTL) in mice to protect them against implantation of tumour cells.

The Applicant has now surprisingly discovered, after a long period of research, that immunosuppressive or angiogenic factors which have a paracrine action are induced by tumours. These factors, which are soluble, can on the one hand locally prevent the cells of the immune system from acting effectively even if they are stimulated (immunosuppression), and on the other hand ensure nutrition of the cancer cells by activating the proliferation of endothelial cells (angiogenesis).

The phenomenon of escape from the cell immune defences of the host by induction of their paralysis in situ is a strategy used by several cancers and is necessary for their survival. Immunosuppression initially remains localized in the tumour, since the individual is still capable of defence against other attacks, such as infections. However, at a later stage this immunosuppression may spread and become generalized, as demonstrated by the dissemination of metastases and the high vulnerability of cancer patients to infections, to say nothing of the debilitating effects due to chemotherapy or radiotherapy. Summarizing, this escape from the control of the immune system is due to a paralysis of the immune system (immunosuppression) which prevents normal functioning. This immunosuppression involves paralysing factors which are produced by the cancer cells or their environment. Local paralysis of cells of the immune system or immunosuppression thus represents a major weapon of cancer cells which enables them to escape from the immune system of the host. Proteins released by the infected cells thus act as true toxins on the surrounding immunity cells, disturb them and block in situ (in a paracrine manner) the cells of the immune system, protecting the infected cells.

Malignant tumours are characterized by the presence of significant vascularization, which ensures an inflow of blood necessary for nutrition of the cancer cells. This vascularization is realized by activation of the induced vascular endothelial cells in contact with the tumour cells (neoangiogenesis). The works of Judah Folkman have recently demonstrated that control of tumour neoangiogenesis could represent a decisive effective weapon against cancers (Folkman J., *Semin. Cancer Biol.*, 1992, 3 (2): 65-71).

In this physiopathological context, the Applicant has discovered, after a long period of research, three proteins involved in local immunosuppression at the level of the tumour in the case of ATL, cancer of the cervix and Kaposi's sarcoma: these are the protein Tax of HTLV-1, the protein E7 of the papilloma virus, and the protein Tat of HIV-1 in Kaposi's sarcoma. In this last case, an immunosuppressive protein of HHV-8 is also said to exist, which would explain how Kaposi's sarcoma also occurs in subjects not infected by HIV-1. Tat has been implicated in Kaposi's sarcoma, but without researchers identifying its role as a generator of local immunosuppression promoting generation of Kaposi's sarcomas. Interestingly, the Applicant has found that some of these immunosuppressive proteins, such as the protein Tat of HIV-1 and the protein E7 of HPV (strains 16 and 18) also have activating effects on vascular endothelial cells.

The object of the present invention is to block, by means of specific antibodies, the soluble factors released by tumour cells or cells infected by a virus. "Soluble factors" are understood as meaning factors (in general proteins) synthesized by the cells and released into the extracellular medium either by active transportation or by passive diffusion. The abovementioned extracellular factors can act in situ either by inhibiting the immunity cell response, including activation of cytolytic T lymphocytes (CTL), or by disturbing the cytokine network, or by satisfying the nutritional requirements of the tumour by neoangiogenesis. These extracellular factors can be of cell origin (cytokines) or, for cancers induced by viruses or viral diseases, viral proteins, chiefly regulatory proteins, present in the extracellular medium.

The present invention describes in particular means of obtaining, in the circulating medium, antibodies directed specifically against deleterious, for example immunosuppressive and/or angiogenic, factors, the said antibodies being capable of blocking these factors and neutralizing the effects on the immunity and/or endothelial cells. These specific antibodies will be either induced by active immunization (vaccination) directed against the proteins, in particular the soluble factors identified beforehand, or administered passively (passive immunization). The circulating antibodies present in the extracellular medium will be able to neutralize the undesirable effects by combining with these proteins.

The Applicant has identified such soluble factors in at least three virus-induced cancers: Kaposi's sarcoma (HIV-1), cancer of the cervix (HPV) and ATL leukaemia (HTLV-1 and -2). These 3 factors, all of viral origin, are, respectively, the protein Tat of HIV-1, the protein E7 of HPV and the protein Tax of HTLV-1.

Several cancers are induced by viruses, such as the HIV-1 responsible for Kaposi's sarcoma and other cancers, the HPV at the origin of cancer of the cervix, and the HBV and EBV associated, respectively, with hepatoma and Burkitt's disease.

The AIDS (Acquired Immunodeficiency Syndrome) disease due to HIV-1 and characterized by a generalized cellular immunosuppression can manifest itself by Kaposi's sarcoma, vascular cancer or by other forms of cancer, including certain leukaemias or lymphomas. The cell immunosuppression observed with this disease which promotes the occurrence of these cancers is induced by the regulatory protein Tat of HIV-1, which, although it does not belong to the actual structure of the virus, is released by the infected cells into the extracellular medium. In this extracellular form, the protein Tat, acting as a true viral toxin, exerts an immunosuppressive effect on the neighbouring immunity cells (Zagury D. et al.; *PNAS*, 1998, 95: 3851-56). Furthermore, at the level of Kaposi's sarcoma, it has been shown that the protein Tat in combination with inflammatory cytokines (IFNα, Il-1, TNFα) and with BFGF, promoted the neoangiogenesis which forms the tumour (Ensoli B. *J. Virol.* 1993, 67: 277-287).

In fact, because of its immunosuppressive and angiogenic properties, the protein Tat present in the extracellular medium promotes in cases of the AIDS disease not only the development of Kaposi's sarcoma caused by the virus HHV-8, but also that of other cancers, including lymphomas or leukaemias.

The epithelial cancer of the cervix is caused by certain strains of the HPV virus (strains 16 and 18). The cancer cells of this cancer express only 2 proteins of early appearance from this virus, the protein E6 and the protein E7, which both have effects on the regulatory factors of the cell cycle of the cancer cell. In addition, the protein E7 present in the extracellular medium explains the occurrence of low levels of antibodies against E7 in patients. The extracellular protein E7, like the extracellular protein Tat, can act locally as a toxin on the stromal cells (lymphoid cells or endothelial cells) of the tumour.

This protein E7 has in fact shown immunosuppressive and angiogenic properties in experiments. The immunosuppression induced by the protein E7 was characterized by inhibition of the proliferation of T cells stimulated by PPD or tetanus toxoid, inhibition of the proliferation of T cells stimulated by allogenic cells, and over-production of IFNα (immunosuppressive cytokine) by antigen-presenting cells (APC). The angiogenic potency of the toxin E7 on cultures of endothelial cells originating from the umbilical cord of neonates and pretreated with the protein E7 was suggested by the following observations: formation of several cell nests, visible by phase contrast; identification by FACS of CAM markers (ICAM and VCAM) within endothelial cells and modification of the cytoskeletons of cells in culture observed by immunofluorescence and alteration of the expression of nitrogen monoxide synthase which can be induced by endothelial cells in culture in the presence of the protein E7. As will be seen more decisively in the examples, the angiogenic potency of the toxin E7 can be demonstrated directly "in vitro" by activation of vascular endothelial cells originating from cell lines or fresh cells of the umbilical cord of neonates induced by the protein E7 of HPV (strain 16).

The induction of antibodies directed against extracellular viral factors, such as the proteins Tat, E7 or Tax, as toxins on the lymphoid stromal or intratumoral endothelial cells, involves the preparation of immunogens biologically deprived of the deleterious effects of the native protein. As a result of their properties, such immunogens or the specific antibodies which they induce can combat the immunosuppression and/or angiogenesis present within tumours and can thus be used as anticancer medicaments.

The present Application chiefly relates to the use:
  of a new product obtained from a natural protein which will be modified by any technique, such as by a chemical or physical (including the galenical form) route or by genetic engineering, such that its immunosuppressive properties are inactivated to the extent of at least 70%, preferably to the extent of at least 90%, in particular to the extent of at least 95%, by a chemical or physical treatment and/or by suitable genetic construction.
  of an antibody against an immunopathogenic, in particular immunosuppressive or angiogenic, protein which has a local action and is induced by a cancer cell or a cell infected by a virus, to obtain a medicament intended for use as a local anti-immunosuppression agent and/or as an anti-angiogenic agent having a local action. Since cancers can proliferate as a result of the local immunosuppression described above and of angiogenesis, the above products are used in part to obtain a medicament intended for use as an anticancer agent.

The abovementioned natural protein is characterized in that it is an initially immunosuppressive and/or angiogenic protein which has a local action and is induced by cancer cells or by cells infected by a virus, or a fragment of these proteins.

The present Application thus relates to the use of a protein originating from cancer cells, cells infected by a virus or immunity cells, or a fragment of this protein, characterized in that this protein is an initially immunosuppressive and/or angiogenic protein which has a local action and in that these properties are rendered inactive to the extent of at least 70%, preferably to the extent of at least 90%, in particular to the extent of at least 95%, by a physical and/or chemical treatment, such as formolation, carboxamidation, maleimidation or oxidation by bubbling oxygen through, by genetic recombination or by an adjuvant make-up, the said treatment preserving the property of being recognized by antibodies directed against the said protein and preserving immunogenic properties sufficient to generate antibodies which neutralize or block the said native protein, to obtain a medicament intended for use as a local anti-immunosuppression or anti-angiogenic agent, as an anticancer agent. "Anti-immunosuppression or anti-angiogenic agent" is understood as meaning that the agent can have one, the other or both effects.

The proteins which have been rendered inactive of the present invention, sometimes called "inactivated proteins" or "toxoids" in the following, allow combating of cancers by an approach which is complementary to those of the prior art and specific, aimed at the paralysis of the immune system and/or the angiogenesis induced by extracellular substances produced locally in the environment of the cancer cells. This immunity paralysis and/or angiogenesis constitutes a true protective barrier and/or a source of nutrition for the tumour.

The proteins which have been rendered inactive of the present invention allow combating in the first instance of these immunosuppressive and/or angiogenic factors by formation of antibodies against these proteins, and in particular against these soluble factors, in order to allow the immune system to act effectively and/or to block neoangiogenesis.

It is important to use the deleterious extracellular factors in a physically, chemically and/or genetically modified (inactivated) and non-native (or non-natural) form so that it no longer exerts its harmful effects (paracrine paralysis of the immune system or local angiogenesis).

The physical treatments can be carried out by means of heat, UV radiation, X-rays or contact with an atmosphere rich in $O_2$. These physical treatments, which generate intramolecular modifications between chemical radicals (for example thiol groupings), can appropriately change the conformation of the molecule and inactivate it functionally, while preserving its immunogenic properties.

The chemical treatment can be carried out with the aid of a coupling agent, such as a dialdehyde, or a carrier protein activated by pretreatment with the aid of a dialdehyde, preferably glutaraldehyde. The chemical treatment can be carried out using a monoaldehyde, in particular formaldehyde. Reference may be made to the disclosure of WO-A-96/27389 in this respect.

The chemical treatment can be carried out, in particular, by other processes, such as carboxymethylation. An example of the carboxymethylation technique is illustrated below in the experimental part. The chemical treatment can also be carried out by N-ethylmaleimidation, with or without glutaraldehydation.

The immunogen can be inactivated as a result of a galenical presentation within an oily liquid, such as incomplete Freund's adjuvant, or which is capable of modifying the non-covalent bonds (electrostatic forces, Van der Waals forces or hydrogen bonds) necessary for its toxic effects.

The genetic modifications can be obtained by genetic engineering using insertions, deletions or substitutions of radicals, operations which are intended to reduce or suppress the deleterious functional sites of the natural molecule. The genetic mutants could optionally be subjected to a complementary chemical and/or physical treatment. The above modified proteins can be prepared, for example, from a protein having a sequence identical or similar to a peptide sequence of an immunopathogenic, in particular immunosuppressive or angiogenic, protein, such as the protein Tat of HIV-1, the protein E7 of the papilloma virus or the protein Tax of HTLV-1, or of a fragment of these proteins and can be obtained, for example, by conventional peptide synthesis on a resin or by genetic engineering. All these processes are well-known in the prior art.

In order to verify that the native immunosuppressive and/or angiogenic protein is recognized properly by antibodies directed against the said modified immunosuppressive protein or its modified fragment according to the invention, the formation of antigen-antibody complexes can be verified, for example, immunologically by ELISA in the presence of specific antibodies, as will be seen below in the experimental part.

Under the preferred conditions of use, the immunogenic compound originates from a native compound (protein or polypeptide fragment) treated with an aldehyde or carboxamidated or maleimidated.

In order to determine whether the immunogenic properties of the modified immunosuppressive and/or angiogenic protein or of a fragment of this protein have been preserved sufficiently (that is to say whether it has been inactivated but not denatured) to create antibodies which block the effects of the said native protein, it is possible, for example, to immunize mammals (rabbits, rats, mice) with the aid of an immunogenic compound according to the invention and to verify that the antibodies produced neutralize the immunosuppressive or angiogenic activities of the protein, as will be seen for the protein Tat of HIV-1, the protein E7 of the papilloma virus and the protein Tax of HTLV-1 in the experimental part.

In order to determine whether the modified immunosuppressive protein or the fragment has lost at least the desired proportion of its immunosuppressive properties, it is possible, for example, to study the effect of the immunosuppressive protein on immunosuppression of human peripheral blood mononuclear cells (PBMC).

The modified and immunogenic immunosuppressive or angiogenic proteins can be derived from any one of the proteins, in particular immunosuppressive proteins, which have a local action and are induced by tumours; reference is made in particular to the protein Tat of the virus HIV-1, the protein E7 of the papilloma virus or the protein Tax of the virus HTLV-1. Reference is also made to the mannan-dependent lectin produced by activated immunity cells.

"Derived" or "to derive" from an immunopathogenic, in particular immunosuppressive or angiogenic, protein which has a local action as is produced by cancer cells or cells infected by a virus or produced by immunity cells is understood as meaning that the immunogenic compound can be made up of all or a fragment of the immunopathogenic, in particular immunosuppressive or angiogenic, starting protein.

It can include one or more modifications in the amino acids of this protein or fragment, such as deletions, substitutions, additions or functionalizations, such as acylation of amino acids, to the extent that these modifications remain within the context defined above (absence of toxicity, immunological characteristics). For example, the replacement of a leucine radical by an isoleucine residue in general does not modify such properties; the modifications must generally affect less than 40% of the amino acids, preferably less than 20% and more particularly less than 10% of the immunopathogenic, in particular immunosuppressive or angiogenic, protein. It is important that the protein or modified fragment is not denatured, as can be effected, for example, by a physical treatment, such as heat, in order to preserve its conformational sites, so that the antibodies induced by the modified derivatives are active with respect to the native protein.

Under preferred conditions, the immunogenic compounds of the invention comprise at least 50% of the entirety or of a segment of the immunopathogenic, in particular immunosuppressive or angiogenic, protein, preferably at least 70%, in particular at least 90%, and more particularly the entirety or virtually the entirety of the said immunosuppressive protein or of the angiogenic protein.

Generally, as regards the modifications, homology or similarity between the modified immunogen and the native immunosuppressive protein or part thereof, as well as the dimensions of the immunogenic compound, and furthermore the methods of use or the coupling of the immunogenic compound according to the invention to an immunogenic protein, such as the tetanus toxoid, reference may be made in particular to WO-A-86/06 414 or to EP-A-0.220.273 or to PCT/US.86/00831, which are equivalents, the disclosure of which is incorporated here by reference.

The present invention also relates to an immunogenic compound, characterized in that it is an initially immunosuppressive and/or angiogenic protein which has a local action and originates from cancer cells, cells infected by a virus or immunity cells, or a fragment of this protein, and in that its immunosuppressive and/or angiogenic properties are inactivated to the extent of at least 70% by a physical and/or chemical treatment, by genetic recombination or by an adjuvant make-up, the said treatment preserving the property of being recognized by antibodies directed against the said protein and preserving immunogenic properties sufficient to generate antibodies which neutralize or block the said native protein, with the exception of carboxymethylated Tat of HIV-1 or a fragment of this protein.

Of the above immunogenic compounds, the immunogenic compounds which are characterized in that they are derived from one of the following immunosuppressive and/or angiogenic proteins:

protein Tax of an HTLV-1 virus protein E7 of the papilloma virus mannan-dependent lectin produced by immunity cells, and in particular activated T lymphocytes are preferred An immunogenic compound as defined above which is a product obtained by genetic recombination and has a peptide homology of at least 70% with the proteins Tat of HIV-1, Tax of HTLV-1 or -2 and E7 of HPV or the mannan-dependent lectin produced by activated immunity cells, or with a segment of these proteins, is also preferred.

An immunogenic compound as defined above, characterized in that it is treated with an aldehyde, in that it is carboxamidated or in that it is maleimidated is also preferred.

Finally, an immunogenic compound as defined above, characterized by an adjuvant make-up which renders it biologically inactive, such as an oily emulsion in incomplete Freund's adjuvant (IFA) is preferred.

The desired immunogenic compound can also be derived from a homologous mutant.

The present invention also relates to a process for the preparation of an immunogenic compound as defined above, characterized in that an initially immunosuppressive or angiogenic protein which has a local action and is induced by a cancer tumour or a homologous mutant protein or a fragment of this protein is subjected to a physical or chemical treatment or to genetic recombination and the expected compound is selected and then purified, or a native or inactivated protein is incorporated into an adjuvant make-up. In fact, by galenical make-up of a physiologically active protein, its biological activity can be masked, while preserving its immunogenicity.

The present invention in particular relates to a process for the preparation of an immunogenic compound as defined above, characterized in that a chemical treatment is carried out which comprises treatment with the aid of an aldehyde followed by coupling to a carrier protein, as well as a process, characterized in that a chemical treatment is carried out which comprises a treatment which blocks the SH radicals by carboxamidation, carboxymethylation or maleimidation.

The carboxymethylation reaction enables the thiol groupings (sulfhydryl groupings) present in the cysteine radicals of the amino acid chains to be modified. Carboxymethylation inactivates some toxic functions dependent on SH groupings, as reported for the protein Tat by Frankel et al. Cell vol. 55 (1988). These groupings react with iodoacetic acid or iodoacetamide by an S-carboxymethylation or S-carboxamidomethylation reaction respectively.

The maleimidation reaction also blocks the SH groupings to form S-maleimide complexes.

For example, the protein Tat has 7 cysteines. These cysteines participate in the formation of inter- and intra-chain disulphide bridges and contribute towards the formation of oligomers.

The reaction product is in each case an S-carboxymethylcysteinyl or S-carboxymethylamidocysteinyl radical.

A fragment can comprise 8 to 110 amino acids, for example, preferably 12 to 60 amino acids, and in particular 12 to 40 amino acids. Such a fragment can also comprise, from the C or N terminal sides, 1 to 5 additional amino acids, that is to say different from the original fragment. A fragment must also comprise at least one cysteine in order to be able to undergo the carboxymethylation.

The carboxymethylation reaction can also be carried out with other chemical agents, such as performic acid, 3-bromopropionic acid, ethyleneimine, (2-bromoethyl)-trimethylammonium bromide, 2-bromoethanesulphonate, 1,3-propanesulphone etc.

Under the preferred conditions of carrying out the process described above, the said starting protein or fragment can be in a form which is fused to a marker (FP) or not fused (P). The FP form can modify per se the molecular conformation and as a result modify its activity.

The starting proteins or fragment of the process are known products, inactivation processes of which may have been described by chance in the literature, for example for a structural study, but which have in no case been used as a vaccine, for example for the Tat of HIV-1 by Frankel A. D. et al. (Cellular uptake of the tat protein from human immunodeficiency virus, Cell, 1988, 55: 1189-83), for Tat by Tanaka et al. Int. J. Cancer, 1991, vol 48, pages 623-630, or which have not yet been described, such as the inactivation of the protein E7 described by Speidel et al, Eur. J. Immunol., 1997, 27 pages 2391-2399. These starting proteins may even be commercially available (Immunodiagnostics Inc., Cat# 1002-2) or may be prepared in a conventional manner.

In particular, the above starting proteins or fragments can be prepared by:

1) synthesis by genetic engineering or by biochemical synthesis;

2) purification.

By genetic engineering, the proteins produced can be purified by affinity chromatography using, for example, antibodies directed against the protein or one of its fragments; it is also possible to synthesize the protein fused to a marker (FP) for attachment to an affinity column.

Under other preferred conditions of carrying out the process described above, if the protein or fragment is fused to a marker (FP), it is subjected to:

concentration, for example by ultrafiltration;

desalination, for example by gel filtration;

a treatment with cyanogen bromide or enterokinase to cleave the fusion protein and thus liberate the protein or fragment;

concentration and diafiltration;

cation exchange chromatography;

concentration by ultrafiltration, followed by exclusion gel filtration.

The above reaction with cyanogen bromide allows thioethers to be cleaved. The action of cyanogen bromide on the polypeptide molecules is selective, effecting cleavage at existing methionine radicals. This reaction leads to the formation of 2 polypeptide fragments per methionine radical. This reaction can be advantageously coupled with the carboxymethylation reaction described above, but it is not necessary for the inactivation.

Under other preferred conditions of carrying out the process described above, the expected protein or fragment is prepared in a form coupled with a compound which allows its purification, for example a peptide fragment containing several histidines, preferably in a continuous sequence of 4, 5 or in particular 6 histidines or more, allowing fixing to a nickel column. To the extent that the presence of this compound does not induce toxicity and does not adversely modify the immunogenicity of the protein or fragment, it is not necessary to cleave it after purification. However, under preferred conditions of carrying out the invention, this compound is cleaved to eliminate it.

The modified proteins which are initially in particular immunosuppressive and/or angiogenic proteins which have a local action and are induced by cancer tumours, and fragments, and of which the immunosuppressive properties are inactivated by a suitable treatment, to which the present invention relates, have very interesting pharmacological properties. In particular, they have remarkable properties antagonistic towards the properties of immunosuppressive and/or angiogenic proteins which have a local action and are induced by a cancer tumour.

These properties are illustrated below in the experimental part. They justify the use of the modified proteins described above as a medicament.

The invention thus also relates to medicaments, characterized in that they are made up of immunogenic compounds as defined above, for their use in a method of therapeutic treatment of the human or animal body, as well as the use of such an immunogenic compound for the preparation of a curative or preventive medicament intended for neutralization of the immunosuppressive and/or angiogenic effects of the above immunosuppressive and/or angiogenic proteins, and in particular of the protein Tat of HIV-1, the protein E7 of the papilloma virus and the protein Tax of HTLV-1. In fact, the compounds according to the invention have lost their immunosuppressive properties or their angiogenic properties and can thus be administered to humans, as will be seen below in the experimental part.

The medicaments according to the present invention are employed, for example, in curative treatment of cancers, in particular of cancers induced by viruses such as, for example, the ATL (acute T cell leukaemia) caused by HTLV-1, or the cancer of the cervix caused by the papilloma virus, or the Burkitt's lymphoma or Kaposi's sarcoma caused by viruses of the herpes family, Epstein-Barr (EBV) and HHV-8 respectively.

The immunogenic compounds according to the invention can be used as follows:

An immunogenic compound according to the present invention is administered to a patient, for example by the subcutaneous or intramuscular route, in an amount sufficient to be effective at the therapeutic level, to a subject having need of such a treatment. The dose administered can range, for example, from 10 to 1,000 µg subcutaneously, once a month for three months, and then periodically as a function of the serum level of the antibodies induced, for example every 2-6 months. Two or more different immunogenic molecules could be administered in the same preparation to induce antibodies which neutralize all the deleterious functional sites in the case where a single immunogenic molecule does not carry all the active sites of the toxin or the over-produced cytokine which is to be neutralized.

The invention also relates to pharmaceutical compositions comprising at least one abovementioned immunogenic compound as the active principle.

As medicaments, the immunogenic compounds of the invention can be incorporated into pharmaceutical compositions intended for any conventional route in use in the field of vaccines, in particular the subcutaneous route, the intramuscular route, the intravenous route or the oral route. The administration can take place in a single dose or a dose repeated once or several times after a certain interval of time.

The present Application thus also relates to a curative or preventive pharmaceutical composition, characterized in that it comprises, as the active principle, one or more new immunogenic compounds as defined above, that is to say with the exception of the inactivated Tat protein of HIV-1, or its fragments. The immunogenic compound can be made up by itself or as a mixture with an excipient or mixture of pharmaceutically acceptable excipients, such as an adjuvant.

The present Application more particularly relates to a vaccine comprising, as the immunogen, an immunogenic compound defined above, and in particular an initially immunosuppressive and/or angiogenic protein which has a local action and is induced by a cancer tumour, or a fragment of this protein, the immunosuppressive and/or angiogenic properties of which are inactivated to the extent of at least 70% by a suitable treatment.

The present invention also relates to a process for the preparation of a compound described above, characterized in that the active principle or principles is or are mixed with the acceptable, in particular pharmaceutically acceptable, excipients by methods which are known per se.

Administration of immunogenic compounds according to the invention to a patient corresponds to an active immunotherapy. It may also be of interest to proceed with a passive immunotherapy, that is to say to provide a patient directly with the antibodies he requires to neutralize the harmful effects of the above proteins, for example immunosuppressive proteins which have a local action and are induced by tumours.

These antibodies, for example against immunosuppressive and/or angiogenic proteins, can be obtained conventionally and, by way of example, after immunization of a mammal, human or animal, with the aid of an immunogenic compound as defined above, by cloning human B lymphocytes transformed by the Epstein-Barr virus and then collecting the expected antibodies secreted by the said transformed B lymphocytes, or by genetic recombination from a phage library.

The present Application thus also relates to such processes for the preparation of antibodies against proteins, in particular immunosuppressive and/or angiogenic proteins of a cancer tumour, and in particular antibodies against protein E7 of the papilloma virus or against protein Tax of HTLV-1, and in particular a process for the preparation of an above antibody, characterized in that a mammal is immunized with the aid of an immunogenic compound as defined above and the antibodies formed are then collected.

The present Application also relates to an antibody against an immunosuppressive or angiogenic protein of a cancer tumour, and in particular polyclonal or monoclonal antibodies obtained from mammals immunized with an immunogenic compound defined above, and especially an immunosuppressive or angiogenic protein of a cancer tumour which has been biologically inactivated but is immunogenic, in particular the protein E7 of the papilloma virus or the protein Tax of HTLV-1, or their fragments. These passively administered antibodies, which are either allogenic (human) or xenogenic (animal), could be complete monoclonal or polyclonal antibodies or F(ab')2 or Fab fragments of the antibody.

"Antibodies against an immunosuppressive or angiogenic protein of a cancer tumour" are understood as meaning monoclonal or polyclonal antibodies or F(ab')2 or Fab fragments of these antibodies or antibodies against an immunosuppressive or angiogenic protein of a cancer tumour which are obtained by genetic construction from a phage library.

The xenogenic antibodies originate from animals hyperimmunized with an immunogenic compound according to the invention, in particular with the protein E7 of the papilloma virus or the protein Tax of HTLV-1 or its derivatives (peptide fragments of the protein E7 of the papilloma virus or of the protein Tax of HTLV-1 detoxified according to the invention), and are
either polyclonal, originating from hyperimmunized animals,
or monoclonal, obtained after hybridization by the Kohler and Milstein technique from splenic cells or adenocytes with a myelomatous line, type x63, in particular x63AG3. In this case, horse or rabbit antibodies are preferred.

The present Application also relates to a process for the preparation of antibodies against an immunosuppressive or angiogenic protein of a cancer tumour, characterized in that a mammal, human or animal, is immunized with an immunogenic compound as defined above.

The present invention also relates to a process for the preparation of monoclonal antibodies against an immunosuppressive or angiogenic protein of a cancer tumour, characterized in that B cells originating from individuals immunized with an immunogenic compound according to the present invention are used, the said B cells being transformed by the EBV virus and producing specific antibodies against an immunosuppressive or angiogenic protein of a cancer tumour.

The above EBV+ cells can be cultured to produce the expected antibodies. These cells, as has been seen, originate in particular from patients immunized with a native immunosuppressive or angiogenic protein of a cancer tumour, or with an immunogenic compound according to the invention.

The present Application also relates to a process for the preparation of monoclonal antibodies according to the invention directed against an immunosuppressive or angiogenic protein of a cancer tumour, which is or is not effectively immunosuppressive, characterized in that hybridomas of a mammal, in particular of mice, from splenocytes or adenocytes, in particular of mice immunized with a native immunosuppressive or angiogenic protein or an immunogenic compound according to the invention, and myeloma cells, preferably of the line x63, are prepared by processes wellknown in the prior art (Kohler and Milstein).

The present Application also relates to a process for obtaining antibodies against an immunosuppressive or angiogenic protein of a cancer tumour by the technology of genetic recombination, characterized in that an immunogenic compound as defined above is used as the immunogen.

The present Application also relates to F(ab')2 or Fab fragments of the said antibodies; these can be obtained by enzymatic digestion, for example.

The present invention similarly relates to a process for passive immunization of cancer subjects using specific antibodies against an immunosuppressive or angiogenic protein of a cancer tumour, and specifically against the protein E7 of the papilloma virus or against the protein Tax of HTLV-1, neutralizing or blocking the harmful effects of this protein and being capable of preparation as indicated above, or F(ab')2 or F(ab) fragments of these antibodies.

The present Application also relates to a process for active immunization, characterized in that an immunogenic compound as defined above, advantageously combined with a mineral, oily or synthetic immunity adjuvant, or an immunogenic compound as defined above, advantageously coupled, for example with the aid of a dialdehyde, or combined with a protein which increases its immunogenicity, is used as the immunogen.

These immunizations can be carried out both curatively and preventively.

A derivative of the protein E7 of the papilloma virus or of the protein Tax of HTLV-1 is preferably used as the immunogens for all the processes above and below.

The invention also relates to a pharmaceutical composition comprising, as the curative or preventive active principle, at least one antibody against an immunosuppressive or angiogenic protein of a cancer tumour as defined above or obtained by the above processes.

Finally, the invention relates to the use of an above immunogenic compound or antibody for the preparation of a medicament intended for treatment of the local immunosuppressive effects of a protein, which has a local immunosuppressive or an angiogenic action, of a cancer tumour.

Summarizing, and in particular, the present invention relates to the preventive or curative use in a cancer subject of specific antibodies such as to block the action, in particular immunosuppressive, of a protein, which has a local immunosuppressive or an angiogenic action, of a cancer tumour, and in particular of the protein Tat of HIV-1, of the protein E7 of the papilloma virus or of the protein Tax of HTLV-1. These specific antibodies could originate:

1. from the subject himself, induced by an active immunization (vaccination) with a local immunosuppressive protein of a cancer tumour deprived of the said immunosuppressive effects but immunogenic (the properties capable of inducing the formation of antibodies have been preserved, while the protein is present and prepared in a suitable manner, coupled or not coupled to a "carrier", aggregated or not aggregated, in the presence or absence of an adjuvant) or
2. from a foreign allo- or xenogenic organism, administered to the subject by passive immunization (serotherapy). These antibodies administered passively could be complete monoclonal or polyclonal antibodies or F(ab')2 or Fab fragments of the antibody.

The invention also relates to pharmaceutical compositions.
a) A pharmaceutical composition comprising, as the preventive or curative agent, an initially local immunosuppressive or angiogenic protein of a cancer tumour but deprived of the said immunosuppressive and immunogenic effects, according to the invention.
b) A pharmaceutical composition comprising, as the preventive or curative agent, antibodies against a protein, which has a local immunosuppressive or angiogenic action, of a cancer tumour, which antibodies are produced from organisms immunized against the said protein, or its F(ab')2 or Fab fragments, according to the invention.

The invention also provides a kit comprising a vaccinal pharmaceutical composition which, in addition to the active principle (initially local immunosuppressive or angiogenic protein of a cancer tumour, but deprived of the said immunosuppressive or angiogenic effects and immunogenic, or its derivative or antibodies against a local immunosuppressive or angiogenic protein of a cancer tumour), can comprise an adjuvant and/or another immunogen having anticancer properties.

Finally, the invention provides a pharmaceutical composition in a conventional galenical form. In particular, the active principle according to the invention is combined, in an amount sufficient to be effective from a therapeutic point of view, with a diluent or a carrier which is acceptable from the pharmaceutical point of view.

To reduce the immunosuppressive load produced by the tumour and to improve still further the immune response, this anti-suppressive immunization could be combined with more conventional means aimed at reducing the size of the tumour, such as chemotherapy, radiotherapy, surgical excision or addition of tumour suppressor genes provided by the techniques of gene therapy (DNA carried by viral vectors, lipid vectors etc.) or such as active immunization against proteins without a local immunosuppressive or angiogenic action, such as MAGE or proteins of a structure such as those of the papilloma virus.

It could also be possible to combine other anti-suppressive and/or -angiogenic immunizations, for example by immunizing against cytokines or lectins capable of mediating the suppressive action on the immunity cells, or to combine immunizations against conventional tumoral antigens (non-immunosuppressive or -angiogenic) capable of increasing the cell immunity, in particular killer, response (CTL cells or NK cells) directed against the tumour cells or cells infected by viruses. The advantage of these combinations is that they would allow the immune system to respond better to anti-immunosuppressive immunization and consequently to restore itself to a better degree.

Summarizing, immunization against a paracrine immunosuppressive or angiogenic factor in an inactive but still immunogenic form could be combined with more conventional methods, such as radiotherapy, chemotherapy, surgical excision or treatment with suppressor genes or immunizations against cytokines or lectins produced by immunity cells (T cells or APC) which mediate the immunosuppressive and/or angiogenic action or against tumoral antigens.

In fact, in some cancers of the same viral origin, soluble factors of cell origin, such as cytokines or lectins, can also play a role locally as a mediator of immunosuppression and/or angiogenesis within the tumour. This is the case with IFNα, an immunosuppressive cytokin, over-produced locally within lymphoid tissues infected by HIV in cases of the AIDS disease.

In vitro experiments on blood mononuclear cells (PBMC) infected with HIV-1 has shown that the protein Tat was involved in the over-production by the APC of the immunosuppressive cytokine IFNα. Interestingly, the protein E7 of HPV, like the protein Tat of HIV-1, induces over-production of immunosuppressive IFNα by the APC.

Consequently, the escape from the immune system and/or the angiogenesis of cancers could also be combated by inducing or administering antibodies directed specifically against the cytokines, over-production of which is responsible for immunopathogenesis, in particular immunosuppression, such as IFNα, and/or angiogenesis, such as TNFα, in accordance with the international patent application WO 92/225.

The immunosuppressive effects due to over-production of IFNα in cancers of the AIDS disease and of the cervix, like those due to over-production of TGFB in virus-induced gliomas, could thus be blocked by antibodies directed against these natural cytokines induced by an active immunization (vaccination) using cytokinoids (modified cytokines which are biologically inactive but immunogenic) as the vaccine. Such antibodies could also be administered passively (passive immunization).

The examples and experiments which follow illustrate the present Application.

EXAMPLE 1

Production of the Protein Tat Inactivated by Chemical Treatment

Preparation 2 ml of bacteria deposited at the Collection Nationale de Cultures de Microorganismes [National Collection of Microorganism Cultures] in Paris on 26th Dec. 1997 under no. 1 1964, which is an *E. coli* bacterium into which has been inserted by transfection a recombinant plasmid containing a gene which codes for a polypeptide containing a fragment made up of 6 histidines, combined with the gene of the protein Tat, are cultured in 400 ml of a base culture medium (yeast extract 5 g/l, tryptone 1 g/l, sodium chloride 1 g/l) and 40 ml of a solution 1 ($CaCl_2 2H_2O$: 0.175 g/l, $MgSO_4 7H_2O$: 5.9 g/l, glucose: 6 g/l). The culture is then incubated at 30° C. for 10 hours at 250 rpm.

The above prefermentation is followed by a fermentation under analogous conditions, maintaining the level of dissolved oxygen at a level of 70% of saturation by regulating the stirring. When the optical density measured at 650 nm reaches the value 6, 100 ml of a sterile 3.75% solution of IPTG (isopropyl β-D-thiogalactopyranoside) in deionized water are added. At the same time, the medium is supplemented with a sterile 25% solution of yeast extract. A solution comprising $MgSO_4 7H_2O$: 8.5 g/l, glucose: 300 g/l, $(NH_4)_2SO_4$: 106 g/l, trace elements, is then added, maintaining the glucose concentration above 2 g/l. The bacterial mass is then harvested 4 hours after introduction of the IPTG. Diafiltration is carried out against a buffer of tris 0.1 M, $NaH_2PO_4$ 0.1 M, dithiothreitol 1 mM, pH 8.0, by counter-current filtration (threshold 0.3 μm).

Three liters of the above crude product are lysed by 4 passes under an increased pressure of 500 bar. The lysate is then centrifuged for 15 min at 4° C. and 5,000 rpm. An amount of urea sufficient to obtain an 8 M solution is then added to the supernatant and the pH is adjusted to 8 .

Purification is then carried out by affinity chromatography over a nickel-NTA agarose column (Qiagen), equilibrated beforehand with 600 ml of buffer A (urea 8M, $NaH_2PO_4$ 0.1 M, tris-HCl 0.1 M, DTT 1 mM, pH 8.0). When charged, the column was washed with 250 ml of buffer A. The protein was then eluted using a discontinuous gradient to obtain the expected fusion protein.

The solution obtained in this way is concentrated on an Amicon membrane at a cut-off threshold of 3,000 daltons to give a final concentration of 10 mg/ml. A crude eluate comprising the expected recombinant fusion protein of HIV-1 Tat is obtained in this way.

A Tat fusion protein fused genetically with a peptide fragment rich in histidines, which allows its attachment to nickel for the purpose of purification, was produced in this way.

The eluate obtained in this way will be subjected to the carboxymethylation reaction.

Preparation of the Tat Toxoid

Stage A: Carboxymethylation

A solution of the protein Tat fused to a peptide fragment rich in histidine, prepared in preparation 1 above, is adjusted to obtain the following concentrations: urea 8 M, Tris HCl 0.3 M, dithiothreitol 10 mM, pH 8.4.

2.6 g iodoacetic acid are added to 100 ml of the above solution under an inert atmosphere. This solution is incubated at 37° C. with exclusion of light and under an inert atmosphere for 90 min. The reaction is blocked by addition of 1 ml of 98% β-mercaptoethanol and the incubation is continued for 60 minutes under the same conditions as above.

The solution resulting from the preceding stage is concentrated with the aid of an Amicon concentrator (Cat# 8400) over a YM3 membrane (threshold of 3,000 D) to a concentration of 10 mg/ml.

The product is then desalinated by passage through a Cellufine GH25 column (MATREX), equilibrated with the aid of 300 ml of a solution of urea 4 M, 0.1 M HCl.

Stage B-Purifications

The eluate is then subjected to ultrafiltration and treated with cyanogen bromide to cleave the amino-terminal part of the carboxymethylated product at the level of the methionine. Cyanogen bromide is added in excess under an inert atmosphere in a proportion of about 50 moles of cyanogen bromide per mole of methionine. This solution is kept in a closed container for 24 h at 37° C. The excess cyanogen bromide is driven off by evaporation under reduced pressure.

The solution obtained is then concentrated, subjected to diafiltration against acetic acid-sodium acetate buffer, 0.05 M, pH 5 using an Amicon diafilterer fitted with a YM3 membrane (threshold 3,000 KD). The amount of inactive product obtained in solution is of the order of 450 mg.

This solution is filtered over an SP-Sepharose FF ion exchange column, equilibrated beforehand with 200 ml of buffer A, and the product is eluted by an NaCl gradient.

The eluate is concentrated again by diafiltration in the same Amicon system and the fraction obtained is purified by gel filtration over a Sephacryl S column (Pharmacia), equilibrated with phosphate buffer, pH 7.4. The end product is filtered over a membrane at 0.22 μm and stored at 4° until used.

This product was subjected to the analyses below and was the subject of the pharmacological tests.

Analyses

Total amount of inactivated product analysed by the Bradford test: 150 mg.

Electrophoresis over polyacrylamide gel, sulphododecylsulphate-PAGE, coloration silver (Phast System, Pharmacia, homogeneous 20% gel): single band with a molecular weight compatible with that expected. No other bands detectable at higher or lower weights.

Electrophoresis by isoelectric gradient (Phast System, Pharmacia, GEL IEF 3-9): a single band visible.

Western blot (Phast System, Pharmacia, monoclonal antibody of hybridoma 5G11): a single band observed and absence of aggregated or degraded material.

Biological activity (induction of the CAT gene in the line HELA-HIV-1-LTR CAT): no activity detectable.

Sequencing of the N-terminal part using the standard sequencing technique of Edman with an Applied Biosystem sequencer (model 477A): the first 20 amino acids obtained coincide with the expected sequence.

E-P-V-D-P-R-L-E-P-W-K-H-P-G-S-Q-P-K-T-A (SEQ ID NO:1)

Endotoxins (LAL test in accordance with the protocol of USP XXIII): less than 0.5 endotoxic units per mg of protein.

Sterility (in accordance with the protocol of USP XXIII): corresponds to standards.

Measurement of the degree of substitution: using Ellman's reagent to determine the free sulfhydryl groupings by comparison with a standard curve measuring cysteines. Comparing the native Tat with the carboxymethylated Tat, it is found that only 0.03% of the cysteines remained active in the carboxymethylated Tat, that is to say 1 active cysteine per 3,330 inactive cysteines. A simple calculation shows that to have a Tat molecule with 7 active cysteines under these conditions, several kg of the protein Tat would be necessary. The inactivation is thus virtually total.

This method leads to the production of non-immunosuppressive Tat, called Tat toxoid, as will be seen below.

EXAMPLE 2

Preparation of Mutant Tat Obtained by Genetic Recombination, which is Inactive but Immunogenic The mutant (AA25; Cys versus Gly) is obtained either by mutagenesis using the phage M13 or by a PCR. This mutant, in contrast to the wild-type Tat protein, proved to be inactive in an amount of 1 μg per ml in the CAT assay and in the immunosuppression test on peripheral blood mononuclear cells stimulated by memory antigens (PPD or tetanus toxoid).

EXAMPLE 3

Preparation of the Protein Tat in an Oily Make-Up Rendering it Biologically Inactive 4 ml of oil (incomplete Freund's adjuvant or ISA 51) are pipetted into a flask cooled in an ice-bath. The shaft of a homogenizer, Silverston type, is introduced into the oil, avoiding contact with the walls of the flask. 4 ml of immunogen in aqueous solution, in a fraction of 20 μl for the 1st ml, 250 μl for the 3rd ml and 500 μl for the 4th ml, are then added to the oil. Between each addition the Silverston is activated at 8,000 revolutions per minute for 4 to 5 seconds, and after addition of all of the aqueous solution for 6 minutes at 8,000 revolutions per minute. A stable water-in-oil emulsion is obtained in this way. In this make-up, the protein Tat, although still immunogenic, proves to be biologically inactive. In vivo, subcutaneous administration of an emulsion comprising 100 μg of Tat has harmful effects neither systemically (curve of weight: temperature) nor on the immune system (normal proliferative cell response of splenocytes stimulated by the memory antigens). In vitro, the protein Tat contained in the aqueous phase isolated from the emulsion proved to be antigenic by the ELISA test but functionally inactive in the CAT assay test.

EXAMPLE 4

Production of the Protein E7 of HPV (Strain 16) by Cells of the Line SIHA, the Genome of which Contains One Copy per Cell of the DNA which Codes for this Protein Cells of the line SIHA cultured in MEM medium comprising 10% FCS are concentrated to $5 \times 10^6$/ml and incubated with or without serum at 37° C. in the presence of 5% $CO_2$ for 18 hours. At the end of this incubation the viability of the cells is greater than 85%. On a smear, after Giemsa staining, these cells are morphologically normal. With reference to cells before incubation, their cytoplasm looks more basophile, the nucleus accommodates one or more large nucleoli and the mitoses are less numerous or non-existent. These cells export into the culture supernatant measurable amounts of the protein E7 which are identified specifically by the immunoblot test using rabbit antibodies against E7 revealed by ELISA. With reference to immuno-prints made on known decreasing amounts of purified recombinant protein E7, these cells in culture have produced amounts of E7 greater than 10 pg/ml in the extracellular medium.

EXAMPLE 5

Production of Protein E7 Inactivated by Chemical Treatment

Tests using glutaraldehyde have allowed production of a protein E7 which is inactivated in the immunosuppression tests. Treatment with glutaraldehyde is carried out in the following manner: to a solution of E7 of 1 mg/ml in disodium phosphate, 70 mM at pH 8.2, is added glutaraldehyde at a final concentration of 0.026 M or 0.0026 M. The reaction is allowed to proceed over varying periods of time ranging from 1 min to 3 hours at room temperature. At the end of each reaction time the reaction is blocked by addition of glycine at a final concentration of 100 mM. The various samples are dialysed for 16 h at 4° C. against 100 times their volume of PBS. The dialysis is repeated twice. It is found in all cases that from after 1 hour of treatment with glutaraldehyde the immunosuppressive of E7 has disappeared, as measured in the immunosuppression test. It is appropriate to optimize the reaction conditions in order to keep the immunogenicity of the protein at a maximum: this is effected by testing the preparations by the method used in experiment 3.

Tests were also carried out with formaldehyde at a final concentration of 33 mM and the inactivation is tested at from 1 hour to several days. The reaction is blocked by addition of glycine, before repeated dialysis against PBS is carried out. The protein obtained, or the E7 toxoid, in contrast to the native protein, showed no immunosuppressive activity in the activity test on peripheral blood mononuclear cells activated by memory antigens (PPD and tetanus toxoid).

EXAMPLE 6

Production of Protein Tax Inactivated by Chemical Treatment

The protein Tax was produced by genetic engineering and obtained at a concentration of 1 mg/ml. Use of the same inactivation protocol using carboxamidation led to the production of a product derived from the Tax toxoid which is inactive in the immunosuppression test on blood mononuclear cells stimulated by memory antigens (PPD and tetanus toxoid).

EXAMPLE 7

| | |
|---|---|
| An injectable composition was prepared, corresponding to the formula composed in example 1 | 50 µg |
| excipient q.s. for a final vial of | 0.5 ml |
| (detail of the excipient: ISA 51 adjuvant (Seppic)) | |

EXAMPLE 8

| | |
|---|---|
| An injectable composition was prepared corresponding to the formula composed in example 3 | 100 µg |
| excipient q.s. for a final vial of 1 ml | 1 ml |
| (detail of the exigent: aluminium hydroxide (Superfos, Kvistgaard, DK)) | |

Pharmacological Study

EXPERIMENT 1a

Immunosuppressive Properties of Extracellular Protein Factors Originating from Cancer Cells, Cells Infected by Viruses or Immunity Cells 1a1. The protein Tat of HIV-1 was purified at a concentration of 1 mg/ml as prepared by Frankel A. D. et al. (Cellular uptake of the Tat protein from human immunodeficiency virus, Cell, 1988, 55: 1189-93).

Peripheral blood mononuclear cells (PBMCS) are taken from a healthy subject, purified by the Ficoll method and cultured at 1 million cells per ml in microwells in the presence of PPD memory antigens (Mérieux, dilution to 1/1,000) in RPMI, BSA serum 10%. The protein Tat is added in a decreasing dose: 10 mg/ml, 3 mg/ml, 1 mg/ml etc. To obtain more pronounced results, it is sometimes necessary to preincubate the cells for 2 h in RPMI with the Tat protein before addition of the serum, since the protein can sometimes bond to components of the serum and thus inactivate its capacity to act on the cells.

IL-2 is added after 48 h. Finally, after 5 days the cell proliferation is measured in the wells by the test of incorporation of tritiated thymidine. The results are the following:

| Proliferation of the PCBMs (CPM) | |
|---|---|
| Without addition of Tat | 28,000 |
| Tat (10 µg/ml) | 8,000 |
| Tat (3 µg/ml) | 13,000 |
| Tat (1 µg/ml) | 21,000 |
| Tat (0.3 µg/ml) | 26,000 |

1a2. Immunosuppressive cytokines covered by the international patent WO 92/225.

1a3. Immunosuppressive Lectins. We have recently identified a lectin produced by T lymphocytes, the hapten of which is mannan and which is immunosuppressive. The inhibition of the cell immune response is demonstrated 1) by the increase in the production of IFNα, an immunosuppressive cytokine, by the APC. This increase is blocked in the presence of mannan and not blocked in the presence of lactose or fructose; 2) by the inhibition of the proliferation of T lymphocytes, PBMC stimulated by memory antigens (PPD, tetanus toxoid) or by alloantigens.

Experimentally, this lectin was demonstrated in the supernatants of H9 cells cultured on HL1 medium without serum, or of PBMC preactivated by the cytokine IL-2 and cultured on HL1 medium without serum. The culture supernatants were concentrated by diafiltration over a membrane with a cut-off at 10 kDa. These concentrated supernatants have the following properties:

1) agglutination of H9 cells inactivated by mytomycin; this agglutination is prevented by mannan.
2) stimulation, at a low concentration, of the proliferation of H9 cells.
3) inhibition, at a high concentration, of the proliferation of H9 cells.

| Agglutination of fixed cells by supernatants of H9 or PBMCs | | | | | | | |
|---|---|---|---|---|---|---|---|
| | Dilutions of the supernatants | | | | | | |
| | 1/2 | 1/4 | 1/8 | 1/16 | 1/32 | 1/64 | 1/28 |
| HL1 medium > 30 kDa | 0* | 0 | 0 | 0 | 0 | 0 | 0 |
| HL1 medium < 30 kDa | 0 | 0 | 0 | 0 | 0 | 0 | 0 |
| H9 SN > 30 kDa | 4 | 4 | 3 | 2 | 2 | 1 | 0 |
| H9 SN < 30 kDa | 0 | 0 | 0 | 0 | 0 | 0 | 0 |
| PBMC SN > 30 kDa | 4 | 3 | 2 | 1 | 0 | 0 | 0 |
| PBMC SN < 30 kDa | 0 | 0 | 0 | 0 | 0 | 0 | 0 |

*Agglutination scores

| Proliferation of H9 cells in the presence of supernatants rich in lectin | | | | | |
|---|---|---|---|---|---|
| | Dilutions of the supernatants | | | | |
| | 0 | 1/2 | 1/4 | 1/8 | 1/16 |
| HP SN > 30 kDa | 12,000* | 8,000 | 16,000 | 21,000 | 13,500 |
| HP SN < 30 kDa | 12,000 | 12,500 | 11,800 | 12,000 | 12,500 |

*Measured by the test of incorporation of 3H-thymidine (cpm).

These properties allow the factor present in the supernatants due to a lectin to be identified.

The immunosuppressive properties of this lectin could have been related to the fact the action of these supernatants on the APC (dendritic cells, macrophages) in culture activated by IFNγ is objectified by a high increase in the production of IFNα by these cells. However, in parallel with the increase in the production of IFNα, the loss of antiviral potency of IFNα on the VSV when the MDBK cells are pretreated by the culture supernatants is observed.

| Culture supernatant | Neutralization on MDBK (%) |
|---|---|
| control medium | 100 |
| H9 | 50 |
| H9 mannan | 100 |
| PBMC | 40 |
| PBMC mannan | 80 |

| Culture supernatant | Increase in the production of IFNα by activated APC (%) |
|---|---|
| control medium | 100 |
| H9 | 250 |
| PBMC | 300 |

1a4. Case of the protein E7 of the papilloma Virus.

The same experiment as with Tat is carried out with the protein E7 of the papilloma virus, purified by the method of Speidel et al, Eur. J. Immunol, 1997, 27, pages 2391-2399.

The tests of incorporation of 3H-thymidine gave similar results.

| Proliferation of PBMCs (CPM) | |
|---|---|
| Without addition of E7 | 29,000 |
| E7 (10 µg/ml) | 6,000 |
| E7 (3 µg/ml) | 10,000 |
| E7 (1 µg/ml) | 11,000 |
| E7 (0.3 µg/ml) | 16,000 |

1a5. Case of the protein Tax of HTLV-1.

The same experiment as with Tat was also carried out with the purified protein Tax of HTLV-1, obtained by the method of Tanaka et al. Int. J. Cancer, 1991, vol 48, pages 623-630.

The tests of incorporation of 3H-thymidine gave similar results.

| Proliferation of PBMCs (CPM) | |
|---|---|
| Without addition of Tax | 25,000 |
| Tax (10 µg/ml) | 7,000 |
| Tax (3 µg/ml) | 15,000 |
| Tax (1 µg/ml) | 21,000 |
| Tax (0.3 µg/ml) | 26,000 |

These results show that the above native proteins are capable of inducing a dose-dependent immunosuppression and have the capacity for demobilizing the immune system. Angiogenic properties of the protein E7.

EXPERIMENT 2

Angiogenic Properties of Extracellular Protein Factors.

Figure 1:
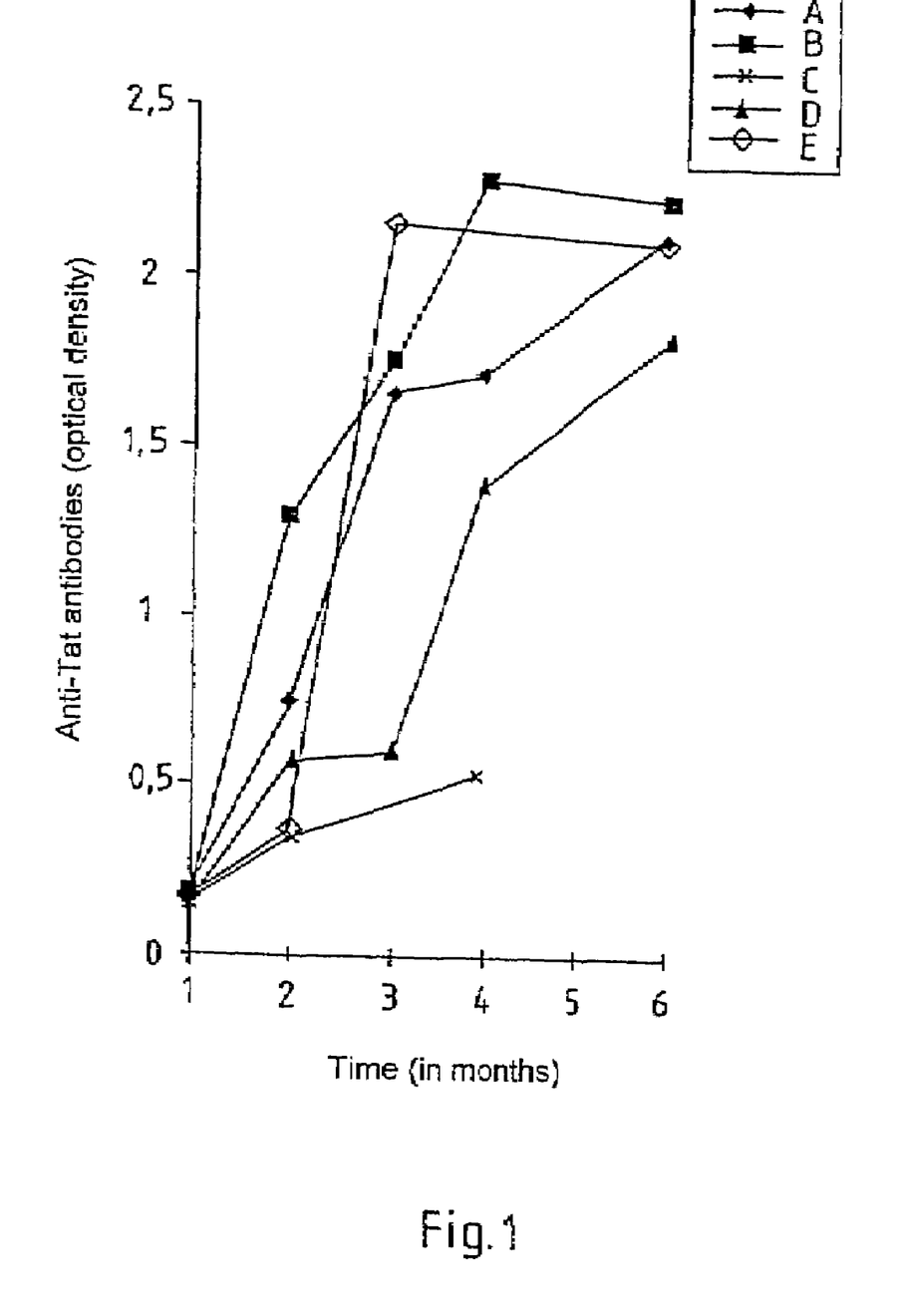
FIG. 1 shows the anti-Tat responses of 5 subjects immunized in experiment 5 below, determined by ELISA on plates referenced by the native protein Tat, after immunization with the Tax toxoid in the 5 subjects and the various repeats.
Figure 2:
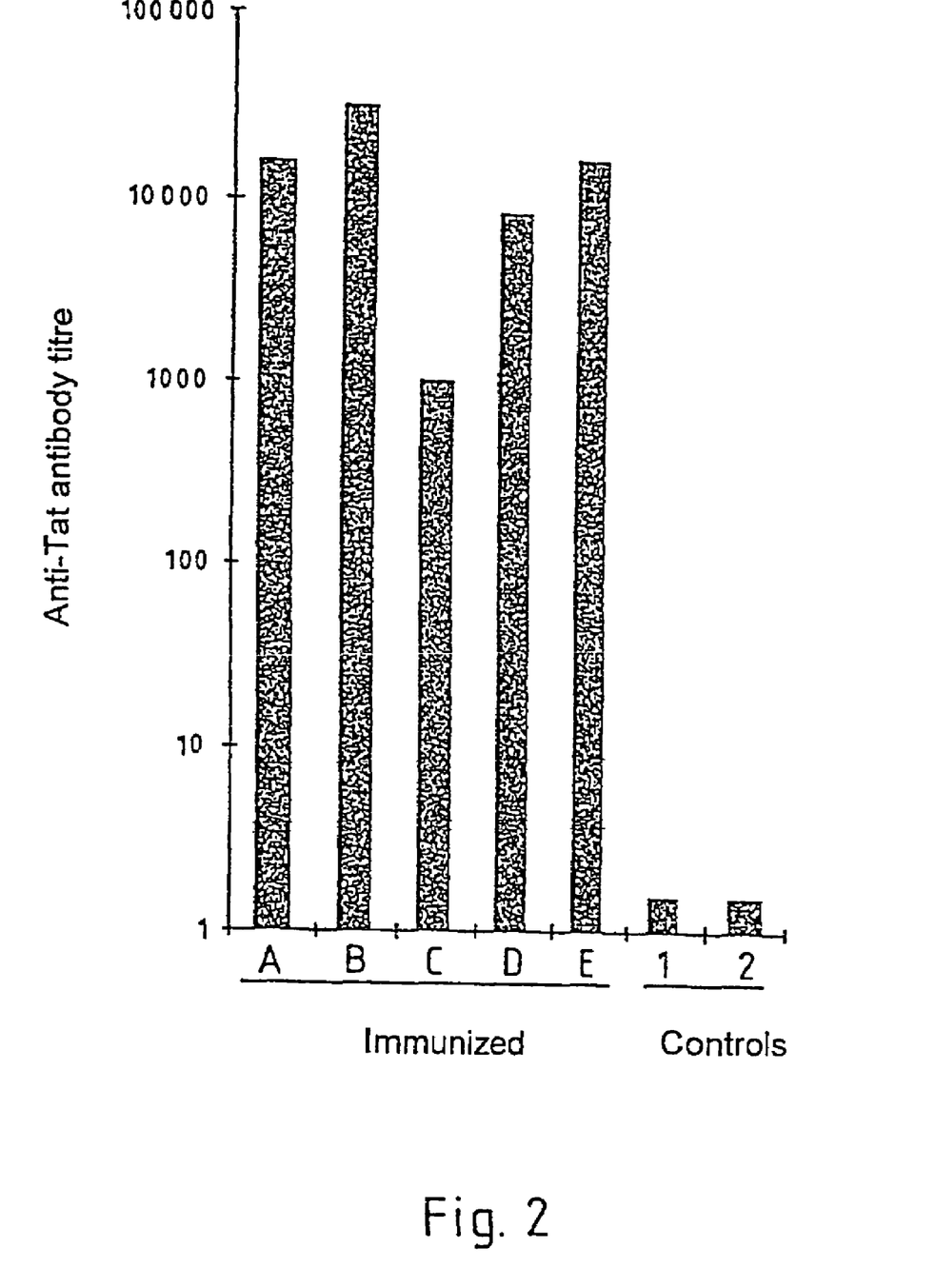
FIG. 2 shows the antibody titres obtained after all the immunizations, in comparison with 2 non-immunized controls.
Figure 3:
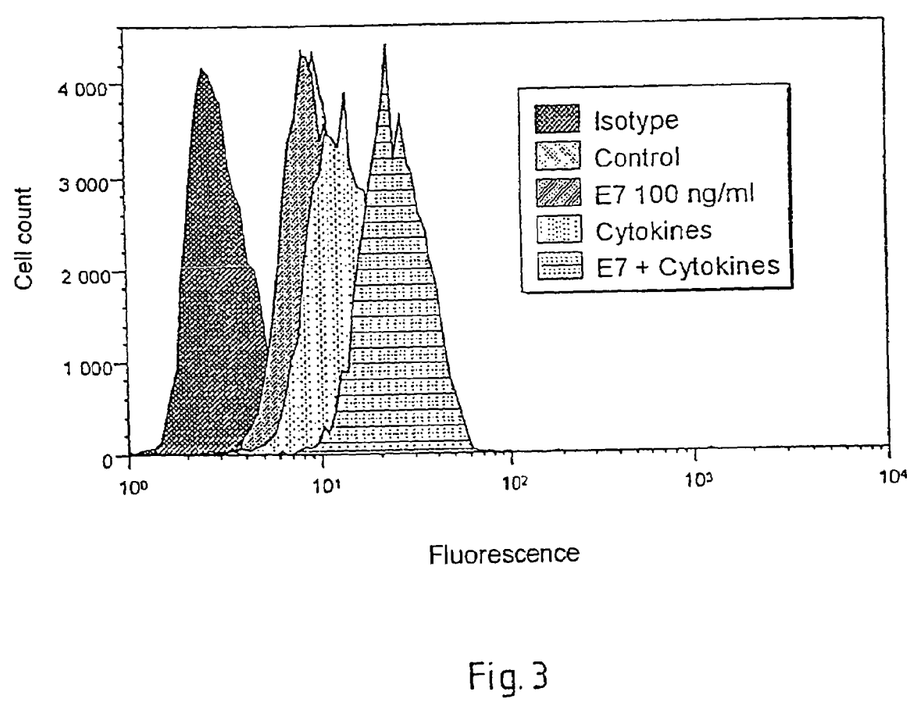
FIG. 3 shows the induction of inducible NO synthase (iNOS) expression in human vascular endothelial cells (HU-VEC) pretreated by the protein $HPV_{16}E7$ and cultured in the presence of cytokines TNFα, IL-1 and IFNγ.
Figure 4:
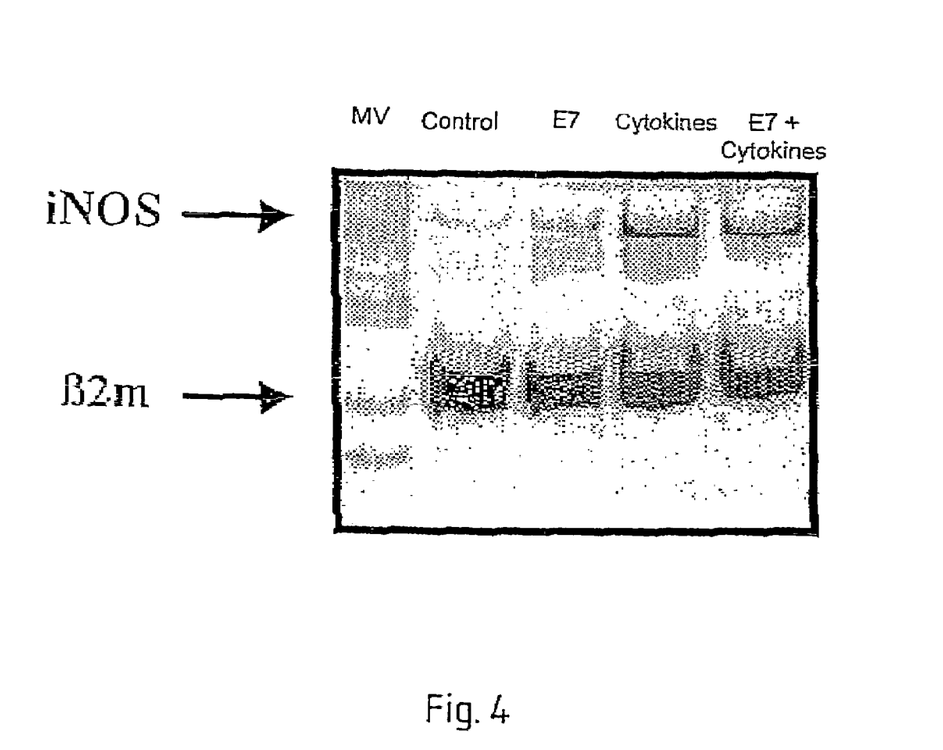
FIG. 4 shows the induction of the messenger RNA of iNOS after 6 hours of treatment with the protein E7 (100 ng/ml) and the cytokines: TNFα (5 ng/ml), IL-1β (1 ng/ml) and IFNγ (1,000 U/ml).
Figure 5:
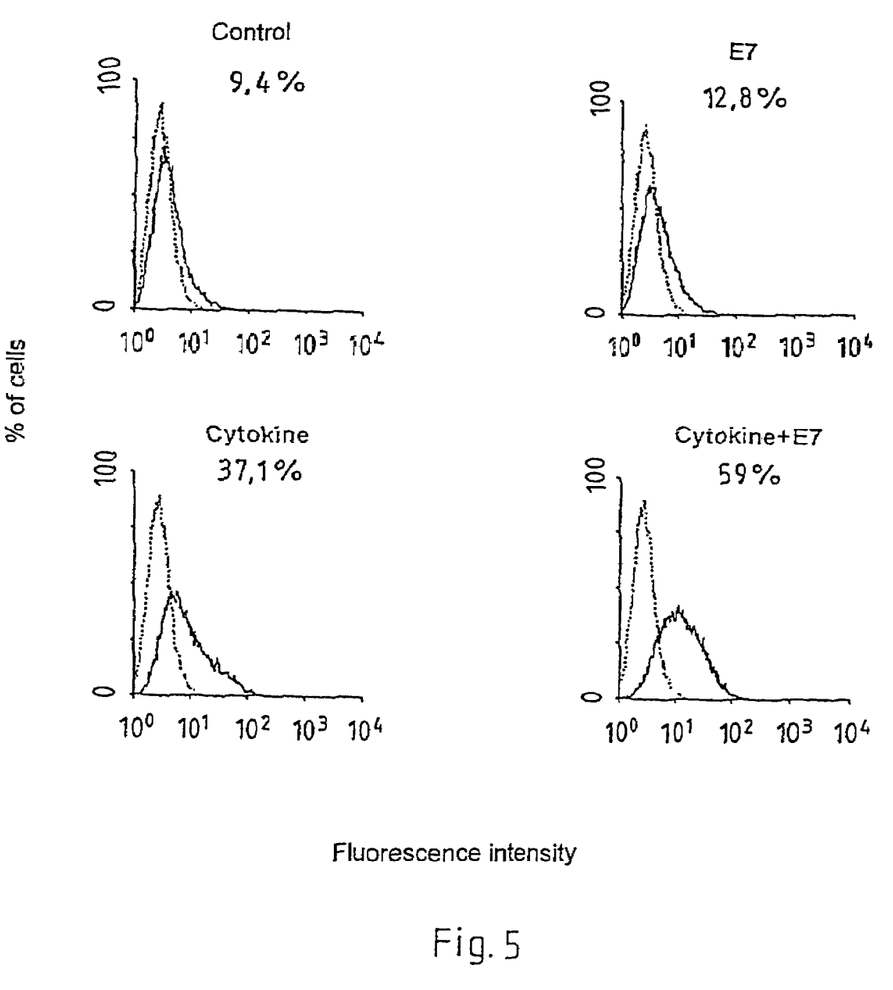
FIG. 5 shows the results of the flow cytometry of human endothelial cells (HUVEC) pretreated or not pretreated with the oncogenic protein E7 and cultured for 12 hours in the presence of cytokines IFNγ, TNFα and IL-1 (effect of the protein E7 on expression of the 1 ICAM-1 adhesion molecule in the endothelial cells of the human umbilical cord).

The purified protein E7 of HPV (strain 16), which significantly increases the production of the cytokines TNFα and IL-1 by macrophages and dendritic cells, also showed angiogenic properties within cultures of endothelial cells originating from the human umbilical cord (HUVEC). In fact, we found that the action of the protein E7 on these cells cultured in a medium comprising EGF, stimulated or not stimulated by the cytokines TNFα, IFNγ or IL-1β, manifested itself by a significant increase in the level of production of NO synthases, as was established by FACS in fluorescence cytometry (FIG. 1) or by a PCR after extraction of the total RNA of cells treated with the protein E7 or the cytokines (FIG. 2). It was also shown that the protein E7, either by itself or in combination with cytokines, significantly increased expression by these same cells of ICAM-1 adhesion molecules (FIG. 3).

EXPERIMENT 3

Absence of Suppressive Activity of Toxoids in the Immunosuppression Test

The proteins modified by chemical treatment of examples 1, 2 and 3 were tested under the same conditions as those described in experiment 1.

No immunosuppressive effect could be demonstrated for these products:

| Proliferation of the PBMCs (% with respect to the control) | |
|---|---|
| Control | 100 |
| Inactivated Tat (10 µg/ml) | 95 |
| Native Tat (10 µg/ml) | 20 |
| Inactivated E7 | 105 |
| Native E7 | 25 |
| Inactivated Tax | 100 |
| Native Tax | 25 |

EXPERIMENT 4

Immunogenicity of the Proteins of Examples 1, 2 and 3

Toxoids prepared according to examples 1, 2 and 3 were used to immunize mice.

The immunization protocol is that conventionally used: The mice are injected (im) with 100 µl of an emulsion (1:1) in complete Freund's adjuvant comprising 20 µg of the product on day 0 with a repeat in incomplete Freund's adjuvant of 5 µg on days 21 and 35. The serum of the mice is sampled on days-2 and 40 and analysed by ELISA on plates sensitized with the corresponding native protein (not chemically treated) and with the toxoids prepared in examples 1, 2 and 3. The sera were tested at a dilution to 1/500.

The results obtained were comparable for the 3 products tested here, Tat toxoid, Tax toxoid and E7 toxoid.

These results, expressed in optical density, obtained on 3 immunized mice (1 to 3) and 3 non-immunized mice (4 to 6) are shown in the following table:

| | Native protein | Inactivated protein |
|---|---|---|
| Mouse 1 | | |
| D-2 | 0.2 | 0.2 |
| D40 | 2.1 | 2.1 |
| Mouse 2 | | |
| D-2 | 0.15 | 0.2 |
| D40 | 2.2 | 2.2 |
| Mouse 3 | | |
| D-2 | 0.2 | 0.1 |
| D40 | 1.9 | 2.1 |
| Mouse 4 | | |
| D-2 | 0.15 | 0.15 |
| D40 | 0.1 | 0.1 |
| Mouse 5 | | |
| D-2 | 0.1 | 0.1 |
| D50 | 0.1 | 0.15 |
| Mouse 6 | | |
| D-2 | 0.2 | 0.2 |
| D40 | 0.1 | 0.1 |

These results show that the mice immunized by the toxoid produce antibodies capable of recognizing the native protein and the toxoid in the same manner. On the other hand, this confirms the innocuity of the immunization with the toxoids, since the mice tolerated the immunization very well.

EXPERIMENT 5

Immunization of Humans with the Product of Example 1

5 seronegative subjects were subjected to immunization with the inactivated immunogenic protein Tat of example 1 in incomplete Freund's adjuvant (ISA 51, Seppic) followed by a first repeat about 3 weeks later and a second repeat about 15 days later. An immune response against the native protein Tat could be objectified by ELISA tests. FIG. 1 shows the anti-Tat responses of the 5 subjects immunized, determined by ELISA on plates referenced with the native protein Tat, after immunization with the Tat toxoid on the 5 subjects and the various repeats. FIG. 2 shows the titres obtained after all the immunizations, compared with 2 non-immunized controls.

It can thus be seen that the toxoid can be used on humans and causes an immune response which produces a cross-reaction with the native protein Tat.

The invention claimed is:

1. An immunogenic polypeptide for inducing antibodies that neutralize the immunosuppressive and/or angiogenic activity of an E7 protein from Papillomavirus, wherein said immunogenic polypeptide consists of an E7 protein from Papillomavirus, or a protein derived therefrom having the sequence of the E7 protein from Papillomavirus except with 10% or less of the amino acid residues being deleted, that has been inactivated, so as to eliminate at least 70% of the immunosuppressive and/or angiogenic activity of the non-inactivated E7 protein, by a chemical treatment selected from the group consisting of treatment carried out with the aid of a coupling agent, treatment carried out with the aid of a carrier protein activated by pre-treatment with a dialdehyde, treatment with a monoaldehyde, carboxymethylation, carboxyamidation, and maleimidation.

2. The immunogenic polypeptide of claim 1, wherein the chemical treatment is treatment carried out with the aid of a coupling agent.

3. The immunogenic polypeptide of claim 2, wherein said coupling agent is a dialdehyde.

4. The immunogenic polypeptide of claim 3, wherein said dialdehyde is glutaraldehyde.

5. The immunogenic polypeptide of claim 1, wherein the chemical treatment is treatment with a monoaldehyde.

6. The immunogenic polypeptide of claim 5, wherein said monoaldehyde is formaldehyde.

7. The immunogenic polypeptide of claim 1, wherein the chemical treatment is carboxyamidation.

8. The immunogenic polypeptide of claim 1, wherein the chemical treatment is carboxymethylation.

9. The immunogenic polypeptide of claim 1, wherein the chemical treatment is maleimidation.

10. The immunogenic polypeptide of claim 1, that has been inactivated by carboxyamidating an E7 protein from Papillomavirus such that the carboxyamidated form thereof is capable of raising antibodies that neutralize the immunosuppressive and/or angiogenic activity of said E7 protein.

11. An immunogenic polypeptide according to claim 1, originating from an E7 protein from Papillomavirus selected from the group consisting of HPV strain 16 and HPV strain 18.

12. A pharmaceutical composition comprising the immunogenic polypeptide of claim 1.

13. An immunogenic composition comprising the immunogenic polypeptide of claim 1, together with at least one adjuvant.

14. A vaccine composition comprising the immunogenic polypeptide of claim 1, together with at least one adjuvant.

* * * * *